United States Patent [19]
Guglielmi et al.

[11] Patent Number: 5,851,206
[45] Date of Patent: Dec. 22, 1998

[54] METHOD AND APPARATUS FOR ENDOVASCULAR THERMAL THROMBOSIS AND THERMAL CANCER TREATMENT

[75] Inventors: Guido Guglielmi, Santa Monica; Cheng Ji, Los Angeles, both of Calif.

[73] Assignee: The Regents of the University of California, Oakland, Calif.

[21] Appl. No.: 497,294

[22] Filed: Jun. 30, 1995

Related U.S. Application Data

[63] Continuation-in-part of Ser. No. 311,508, Sep. 23, 1994, Pat. No. 5,540,680, which is a continuation-in-part of Ser. No. 840,211, Feb. 24, 1992, Pat. No. 5,354,295, which is a continuation-in-part of Ser. No. 492,717, Mar. 13, 1990, Pat. No. 5,122,136.

[51] Int. Cl.$^6$ .................................................... A61B 17/39
[52] U.S. Cl. ............................... 606/28; 606/29; 606/32; 606/41
[58] Field of Search .................................. 606/27–29, 31, 606/32, 41; 607/96, 98, 99, 103, 113

[56] References Cited

U.S. PATENT DOCUMENTS

| | | |
|---|---|---|
| 2,839,049 | 6/1958 | MacLean . |
| 3,789,841 | 2/1974 | Antoshkiw . |
| 3,996,938 | 12/1976 | Clark, III . |
| 4,030,508 | 6/1977 | Thalen . |
| 4,114,603 | 9/1978 | Wilkinson . |
| 4,411,648 | 10/1983 | Davis et al. . |
| 4,512,338 | 4/1985 | Balko et al. . |
| 4,522,205 | 6/1985 | Taylor et al. . |
| 4,538,622 | 9/1985 | Samson et al. . |
| 4,545,390 | 10/1985 | Leary . |
| 4,554,929 | 11/1985 | Samson et al. . |
| 4,567,900 | 2/1986 | Moore . |
| 4,576,174 | 3/1986 | Miyazaki et al. . |
| 4,585,013 | 4/1986 | Harris . |
| 4,613,324 | 9/1986 | Ghajar . |
| 4,619,274 | 10/1986 | Morrison . |
| 4,660,571 | 4/1987 | Hess et al. . |
| 4,723,556 | 2/1988 | Sussman . |
| 4,735,201 | 4/1988 | O'Reilly . |
| 4,739,768 | 4/1988 | Engelson . |
| 4,748,986 | 6/1988 | Morrison et al. . |
| 4,820,298 | 4/1989 | Leveen et al. . |
| 4,884,579 | 12/1989 | Engelson . |
| 4,994,069 | 2/1991 | Ritchart et al. . |
| 5,019,075 | 5/1991 | Spears et al. ............................. 606/28 |

(List continued on next page.)

OTHER PUBLICATIONS

Experiences with surgical thrombosis of intracranial . . . ; Muller; J. Neurosurg./vol. 41/Dec. 1974; pp. 657–670.

Electrothrombosis of carotid–cavernous fistula; Hosobuchi; J. Neurosurg/vol. 42/Jan. 1975; pp. 76–85.

Electrically Induced Thrombosis for the Treatment of Intracranial . . . Araki et al.; Excerpta Medica Intl Congress Series, 1965, vol. 110.

(List continued on next page.)

*Primary Examiner*—Lee S. Cohen
*Attorney, Agent, or Firm*—Daniel L. Dawes

[57] ABSTRACT

A trombus is generated in an aneurysm, arteriovenous malformation or fistula by means of a catheter having an insulated heating coil coupled to an insulated delivery wire. In one embodiment, two delivery wires are coupled to heating coils to provide a closed circuit. The heating coils may be in the form of a double helix or a single helix in combination with a straight heating coil. The heating coils may be electrolytically or mechanically detached therefrom. Alternatively, a single insulated heating coil may be attached to a single insulated delivery wire with a uninsulated coil attached to the tip of the insulated heating coil. The electrical circuit is then made through the heating coil and non-insulated electrode coil into the vascular system and to a body electrode. A catheter may also be used for heating blood within the vascular system which is directly flowed into a tumoral mass for the purposes of thermal treatment of cancer.

19 Claims, 4 Drawing Sheets

U.S. PATENT DOCUMENTS

| | | |
|---|---|---|
| 5,122,136 | 6/1992 | Guglielmi et al. .................... 606/32 |
| 5,178,618 | 1/1993 | Kandarpa .............................. 606/28 |
| 5,217,484 | 6/1993 | Marks . |
| 5,226,911 | 7/1993 | Chee et al. . |

OTHER PUBLICATIONS

Bio–Electric Phenomena as an Etiologic Factor in Intravascular Thrombosis; Sawyer et al.; vol. 175, 1953; pp. 103–107.

Selective vascular thrombosis induced by a direct electrical . . . ; Piton et al.; J. Neurocardiology, 1978, 5, 139–152.

Laser–Induced Thermal Occlusion of Berry Aneurysms:Initial Experimental Results; O'Reilly et al.; Radiology 1989; 171:471–474.

Electrothermic Coagulation of Aortic Aneurysms; Blakemore et al.; vol. 111, No. 20, pp. 1821–1827.

Treatment of Trigeminal Neuralgia by Thermocoagulation . . . ; Fraioli et al.; Neurosurgery, vol. 24, No. 2 pp. 239–245.

Clinical Use of Transcatheter Electrocoagulation; Miller et al.; Work in Progress, vol. 129, 1978 pp. 211–214.

Experimental Closure of Arteriovenous Fistula by Transcatheter Electrocoagulation; Phillips et al.; Radiology 115:319–321, 1975.

Transcatheter Electrocoagulation: A Therapeutic Angiographic Technique for Vessel Occlusion; Thompson et al.; Rad.1977 V12,146–53.

A Simple Method for Preventing Misplaced Electrocauterization; Nichter et al.; Endoscopy 16 (1984) 229–230.

Electrical Potential Differences Across the Normal Aorta . . . of Dogs; Sawyer et al.; vol. 175, pp. 113–117, 1953. Am.J.Physiol.

Relations of Abnormal and Injury Electric Potential Differences . . . ; Sawyer et al.; Am.J.Physiol. pp. 108–112, 1953.

Properties of Electromagnetic Field Focusing Probe; Yamanashi et al.; J.Vascular Diseases,Nov. 1988, pp. 953–959.

Diathermy ERCP; Caletti et al.; Gastrointestinal Endoscopy, vol. 26, No. 1 1980, pp. 13–15.

Experimental Myocardial Infarction; Salazar; Cir. Research, vol. IX, Nov. 1961 pp. 1351–1356.

Natural History of Autologous Blood Clot Embolization in Swine; Osterman et al.; Inv.Radiology 1976 vol. 11, pp. 267–276.

Radiofrequency Current Directed Across the Mitral Anulus . . . ; Jackman et al.; Circulation vol. 78 No. 5 Nov. 1988 pp. 1288–1298.

Experimental production of complete heart block by electrocoagulation . . . ; Beazell et al.; Am Heart J 104:1328, 1982.

Effect of Increasing Current and Decreasing Blood Flow . . . ; Ralston et al.; Inv. Radiology 1982 vol. 17 pp. 171–177.

Catheter for Endoluminal Bipolar Electrocoagulation; Becker et al.; Radiology 1989; 170:561–562.

Intrasaccular Wiring of Abdominalarteriosclerotic Aortic . . . ; Linton; pp. 485–497.

Treatment of Thoracic Aortic Aneurysms by the "Pack" Method . . . ; Linton et al.; N.E.J.M. vol. 246 No. 22, 1952, pp. 847–855.

Aneurysm of the Internal Carotid Artery Within the Skull; Werner et al.; vol. 116, No. 7, 1941.

Electrically Induced Thrombosis in Intracranial Aneurysms; Mullen et al.; pp. 539–547.

An Experimental Approach to the Problem of Cerebral Aneurysm; Mullen et al.; pp. 838–845.

Stereotactic Copper Electric Thrombosis of Intracranial Aneurysms; Mullan et al., Progr.neurol.surg. vol. 3, pp. 193–211.

Vascular Thrombosis Induced by Direct Electric Current; Piton et al.; Neuroradiology 16. 385–388 (1978).

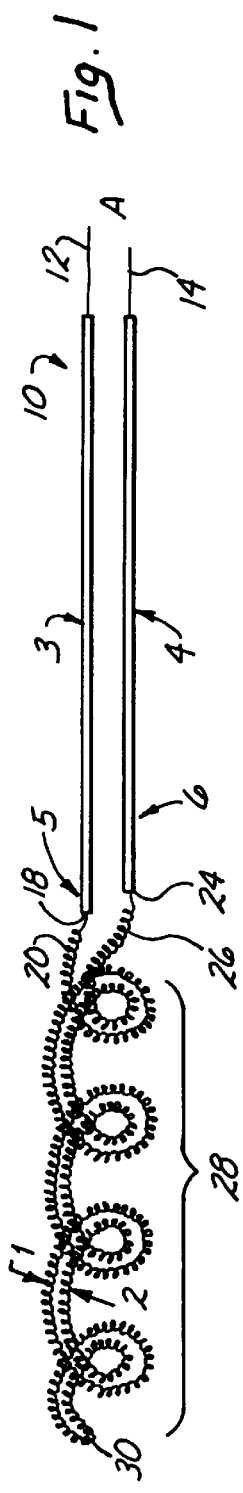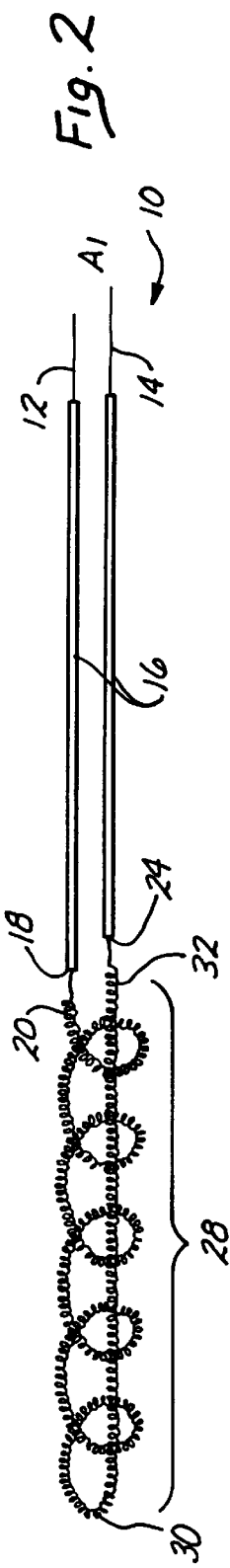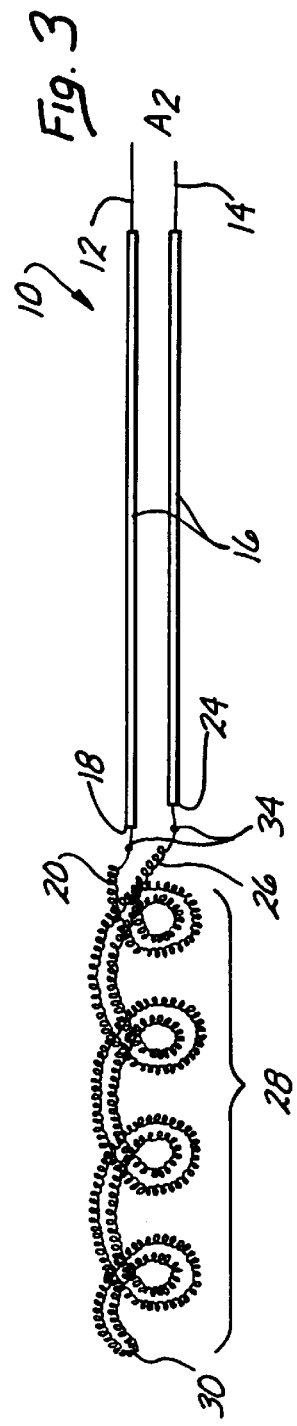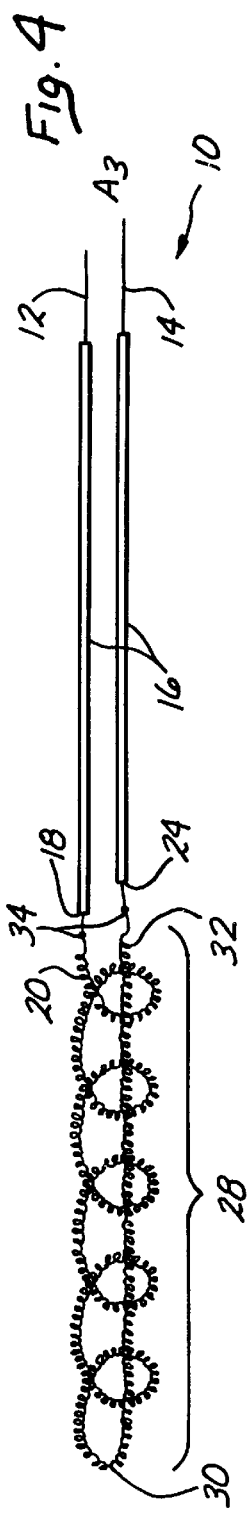

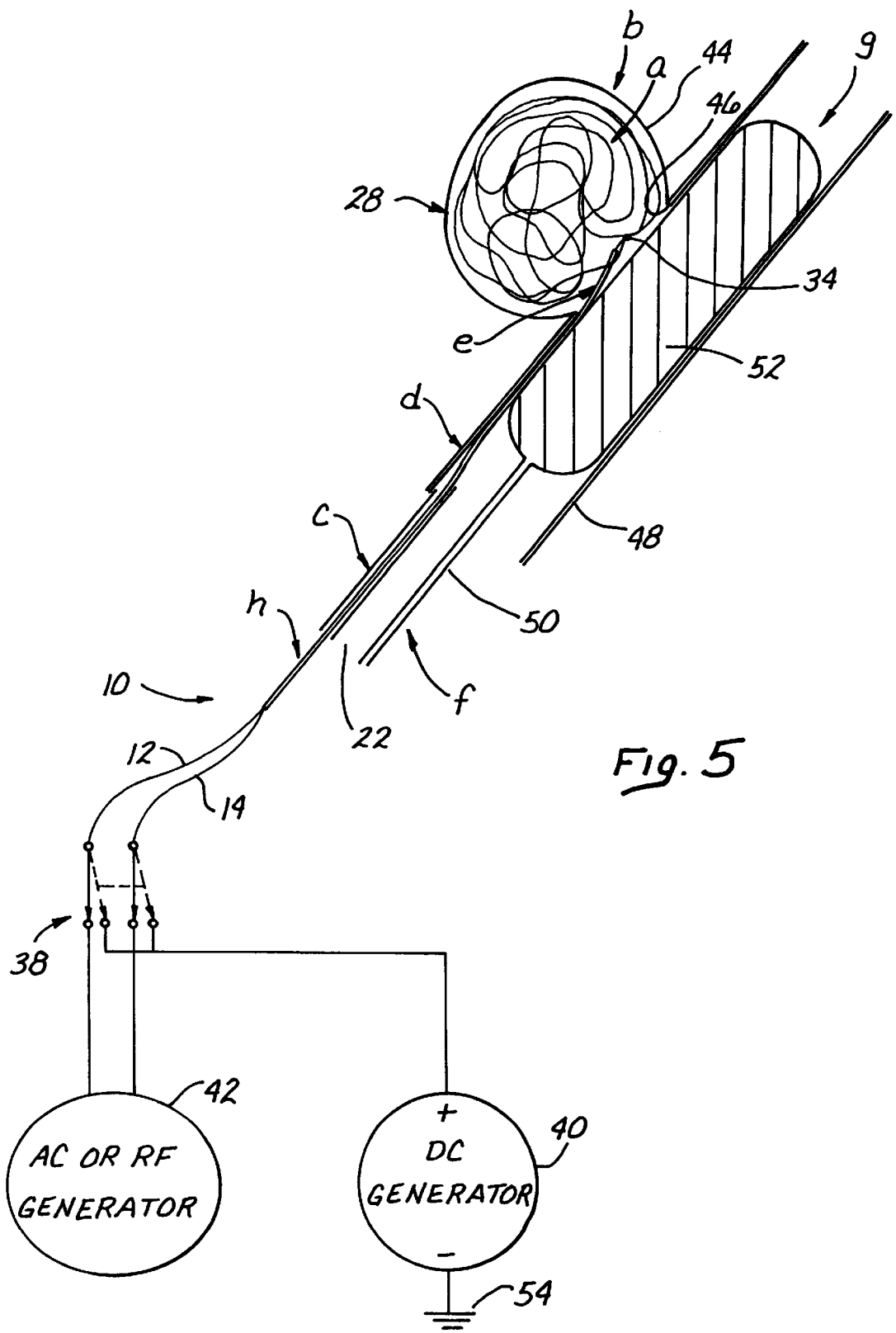

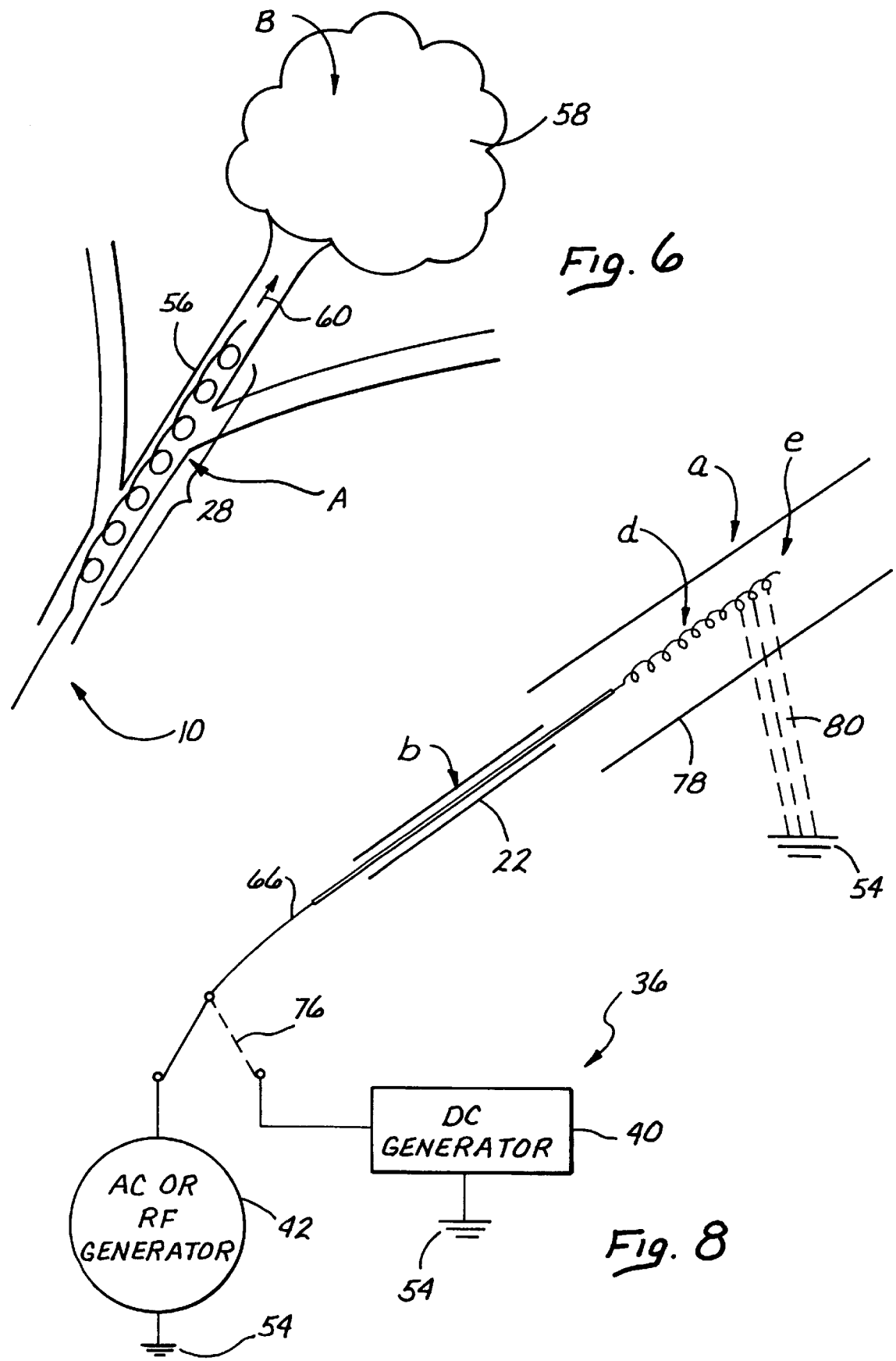

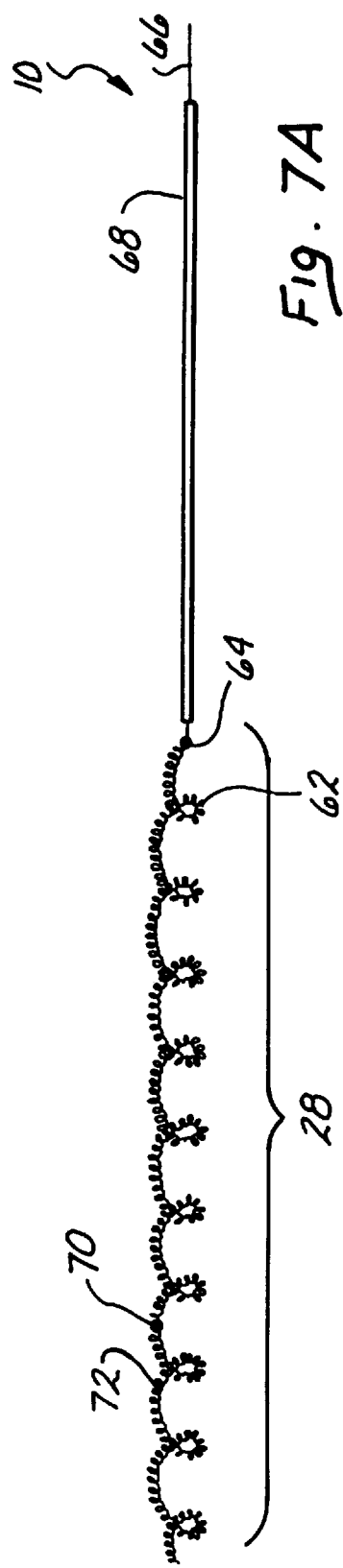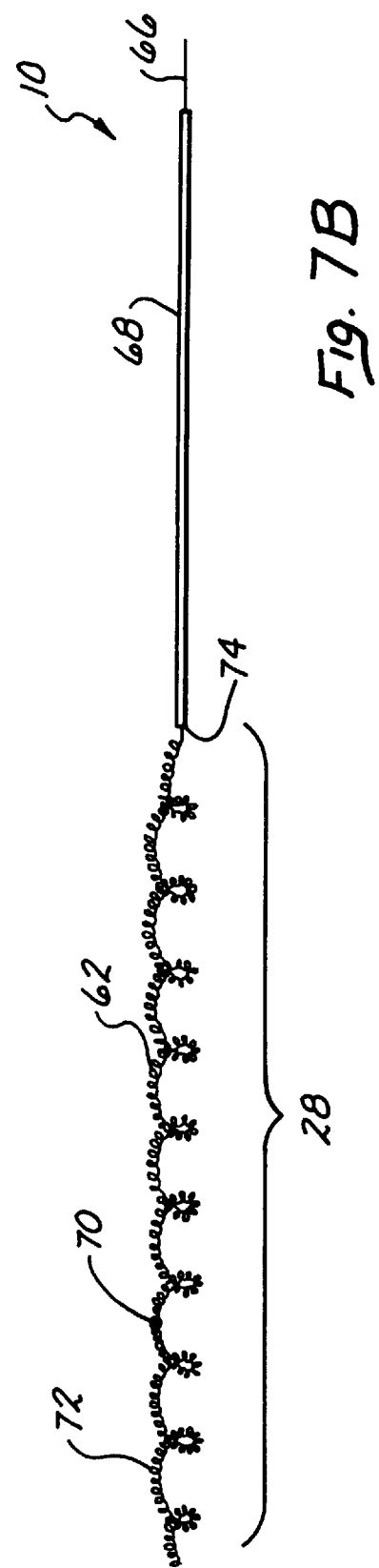

5,851,206

METHOD AND APPARATUS FOR ENDOVASCULAR THERMAL THROMBOSIS AND THERMAL CANCER TREATMENT

RELATED APPLICATIONS

The present application is a continuation-in-part application of U.S. patent application Ser. No. 08/311,508 filed Sep. 23, 1994 and entitled "Improvements in an Endovascular Electrolytically Detachable Wire and Tip for the Formation of Thrombus in Arteries, Veins, Aneurysms, Vascular Malformations, and Arteriouvenous Fistulas", now U.S. Pat. No. 5,540,680, which was a continuation-in-part application of application Ser. No. 840,211, filed Feb. 24, 1992, and issued as U.S. Pat. No. 5,354,295, which in turn was a continuation-in-part application of application Ser. No. 492,717, filed Mar. 13, 1990 and issued as U.S. Pat. No. 5,122,136, all of which are incorporated herein by reference as if set forth in their entirety.

BACKGROUND OF THE INVENTION

1. Field of the Invention

The invention relates to the field of endovascular devices and methodologies and in particular to a means for endovascular heating of blood for purposes of promoting thrombosis in aneurysms, thrombosis in arteriovenous malformations or fistulas, and thermally heating blood in a tumor for consequent destruction of tumoral cells.

2. Description of the Prior Art

Approximately 25,000 intracranial aneurysms rupture every year in North America. The primary purpose of treatment for ruptured intracranial aneurysm is to prevent rebleeding. At the present time, three general methods of treatment exist, namely an extravascular, endovascular and extra-endovascular approach.

The extravascular approach is comprised of surgery or microsurgery of the aneurysm or treatment site for the purpose of preserving the parent artery. This treatment is common with intracranial berry aneurysms. The methodology comprises the step of clipping the neck of the aneurysm, performing a suture-ligation of the neck, or wrapping the entire aneurysm. Each of these surgical procedures is performed by intrusive invasion into the body and performed from outside the aneurysm or target site. General anesthesia, craniotomy, brain retraction and arachnoid dissection around the neck of the aneurysm and placement of a clip are typically required in these surgical procedures. Surgical treatment of vascular intracranial aneurysm can expect a mortality rate of 4–8% with a morbidity rate of 18–20%. Because of the mortality and morbidity rate expected, the surgical procedure is often delayed while waiting for the best surgical time with the result that an additional percentage of patients will die from the underlying disease or defect prior to surgery. For this reason the prior art has sought alternative means of treatment.

In the endovascular approach, the interior of the aneurysm is entered through the use of a microcatheter. Recently developed microcatheters, such as those shown by Engleson, "Catheter Guidewire", U.S. Pat. No. 4,884,579 and as described in Engleson, "Catheter for Guidewire Tracking", U.S. Pat. No. 4,739,768 (1988), allow navigation into the cerebral arteries and entry into a cranial aneurysm.

In such procedures a balloon is typically attached to the end of the microcatheter and it is possible to introduce the balloon into the aneurysm, inflate it, and detach it, leaving it to occlude the sac and neck with preservation of the parent artery. While endovascular balloon embolization of berry aneurysms is an attractive method in situations where an extravascular surgical approach is difficult, inflation of a balloon into the aneurysm carries some risk of aneurysm rupture due to possible over-distention of portions of the sac and due to the traction produced while detaching the balloon.

While remedial procedures exist for treating a ruptured aneurysm during classical extravascular surgery, no satisfactory methodology exists if the aneurysm breaks during an endovascular balloon embolization.

Furthermore, an ideal embolizing agent should adapt itself to the irregular shape of the internal walls of the aneurysm. On the contrary, in a balloon embolization the aneurysmal wall must conform to the shape of the balloon. This may not lead to a satisfactory result and further increases the risk of rupture.

Still further, balloon embolization is not always possible. If the diameter of the deflated balloon is too great to enter the intracerebral arteries, especially in the cases where there is a vasospasm, complications with ruptured intracranial aneurysms may occur. The procedure then must be deferred until the spasm is resolved and this then incurs a risk of rebleeding.

In the extra-intravascular approach, an aneurysm is surgically exposed or stereotaxically reached with a probe. The wall of the aneurysm is then perforated from the outside and various techniques are used to occlude the interior in order to prevent it from rebleeding. These prior art techniques include electrothrombosis, isobutyl-cyanoacrylate embolization, hog-hair embolization and ferromagnetic thrombosis.

In the use of electrothrombosis for extra-intravascular treatment the tip of a positively charged electrode is inserted surgically into the interior of the aneurysm. An application of the positive charge attracts white blood cells, red blood cells, platelets and fibrinogen which are typically negatively charged at the normal pH of the blood. The thrombic mass is then formed in the aneurysm about the tip. Thereafter, the tip is removed. See Mullan, "*Experiences with Surgical Thrombosis of Intracranial Berry Aneurysms and Carotid Cavernous Fistulas*", J. Neurosurg., Vol. 41, December 1974; Hosobuchi, "*Electrothrombosis Carotid-Cavenous Fistula*", J. Neurosurg., Vol. 42, January 1975; Araki et al., "*Electrically Induced Thrombosis for the Treatment of Intracranial Aneurysms and Angiomas*", Excerpta Medica International Congress Series, Amsterdam 1965, Vol. 110, 651–654; Sawyer et al., "*Bio-Electric Phenomena as an Etiological Factor in Intravascular Trombosis*", Am. J. Physiol., Vol. 175, 103–107 (1953); J. Piton et al., "*Selective Vascular Thrombosis Induced by a Direct Electrical Current; Animal Experiments*", J. Neuroradiology, Vol. 5, pages 139–152 (1978). However, each of these techniques involves some type of intrusive procedure to approach the aneurysm from the exterior of the body.

The prior art has also devised the use of a liquid adhesive, isobutyl-cyanoacrylate (IBCA) which polymerizes rapidly on contact with blood to form a firm mass. The liquid adhesive is injected into the aneurysm by puncturing the sac with a small needle. In order to avoid spillage into the parent artery during IBCA injection, blood flow through the parent artery must be momentarily reduced or interrupted. Alternatively, an inflated balloon may be placed in the artery at the level of the neck of the aneurysm for injection. In addition to the risks caused by temporary blockage of the parent artery, the risks of seepage of such a polymerizing adhesive into the parent artery exists, if it is not completely blocked with consequent occlusion of the artery.

Still further, the prior art has utilized an air gun to inject hog hair through the aneurysm wall to induce internal thrombosis. The success of this procedure involves exposing the aneurysm sufficiently to allow air gun injection and has not been convincingly shown as successful for thrombic formations.

Ferromagnetic thrombosis in the prior art in extra-intravascular treatments comprises the stereotactic placement of a magnetic probe against the sac of the aneurysm followed by injection into the aneurysm by an injecting needle of iron microspheres. Aggregation of the microspheres through the extravascular magnet is followed by interneuysmatic thrombus. This treatment has not been entirely successful because of the risk of fragmentation of the metallic thrombus when the extravascular magnet is removed. Suspension of the iron powder in methyl methylmethacrylate has been used to prevent fragmentation. The treatment has not been favored, because of the need to puncture the aneurysm, the risk of occlusion of the parent artery, the use of unusual and expensive equipment, the need for a craniectomy and general anesthesia, and the necessity to penetrate cerebral tissue to reach the aneurysm.

Endovascular coagulation of blood is also well known in the art and a device using laser optically generated heat is shown by O'Reilly, "*Optical Fiber with Attachable Metallic Tip for Intravascular Laser Coagulation of Arteries, Veins, Aneurysms, Vascular Malformation and Arteriovenous Fistulas*", U.S. Pat. No. 4,735,201 (1988). See also, O'Reilly et al., "*Laser Induced Thermal Occlusion of Berry Aneurysms: Initial Experimental Results*", Radiology, Vol. 171, No. 2, pages 471–74 (1989). O'Reilly places a tip into an aneurysm by means of an endovascular microcatheter. The tip is adhesively bonded to a optic fiber disposed through the microcatheter. Optical energy is transmitted along the optic fiber from a remote laser at the proximal end of the microcatheter. The optical energy heats the tip to cauterize the tissue surrounding the neck of the aneurysm or other vascular opening to be occluded. The catheter is provided with a balloon located on or adjacent to its distal end to cut off blood flow to the site to be cauterized and occluded. Normally, the blood flow would carry away the heat at the catheter tip, thereby preventing cauterization. The heat in the tip also serves to melt the adhesive used to secure the tip to the distal end of the optical fiber. If all goes well, the tip can be separated from the optical fiber and left in place in the neck of the aneurysm, provided that the cauterization is complete at the same time as the hot melt adhesive melts.

A thrombus is not formed from the heated tip. Instead, blood tissue surrounding the tip is coagulated. Coagulation is a denaturation of protein to form a connective-like tissue similar to that which occurs when the albumen of an egg is heated and coagulates from a clear running liquid to an opaque white solid. The tissue characteristics and composition of the coagulated tissue is therefore substantially distinct from the thrombosis which is formed by the thrombotic aggregation of white and red blood cells, platelets and fibrinogen. The coagulative tissue is substantially softer than a thrombic mass and can therefore more easily be dislodged.

O'Reilly's device depends at least in part upon the successful cauterization timed to occur no later than the detachment of the heat tip from the optic fiber. The heated tip must also be proportionally sized to the neck of the aneurysm in order to effectively coagulate the tissue surrounding it to form a blockage at the neck. It is believed that the tissue in the interior of the aneurysm remains substantially uncoagulated. In addition, the hot melt adhesive attaching the tip to the optic fiber melts and is dispersed into the adjacent blood tissue where it resolidifies to form free particles within the intracranial blood stream with much the same disadvantages which result from fragmentation of a ferromagnetic electrothrombosis.

Therefore, what is needed is an apparatus and methodology which avoids each of the shortcomings and limitations of the prior art discussed above.

BRIEF SUMMARY OF THE INVENTION

The invention is an improvement in a catheter for use within a vascular system. The improvement comprises at least one delivery wire. At least one heating coil is coupled to the delivery wire. The delivery wire and heating coil are both electrically insulated to permit endovascular disposition of the delivery wire and heating coil into the vascular system for the purpose of delivering heat to a fluid within the vascular system at a predetermined location. Substantially all of the heat is generated by electrical current flowing within the heating coil rather than within the delivery wire, because of the greater electrical resistance of the heating coil. As a result, endovascular thermal treatment is provided within the vascular system.

The delivery wire and heating coil are temporarily coupled to each other and can be selectively detached. In the preferred embodiment the delivery wire and heating coil are electrolytically detachable from each other. However, the delivery wire and heating coil may also be mechanically detachable from each other.

The improvement further comprises at least two delivery wires and at least two heating coils, each having a proximal and distal end. The proximal end of each of the heating coils is coupled to corresponding ones of the two delivery wires. The distal end of the two heating coils is coupled together to provide a continuous circuit through a first one of the two delivery wires to a first one of the two heating coils, to a second one of the two heating coils, and to a second one of the two delivery wires.

In the illustrated embodiment the two heating coils are each helical and together form a double helical tip. In another embodiment one of the two delivery wires is helical and the other one of the two delivery wires is nonhelical.

In another embodiment the improvement further comprises a body electrode in electrical circuit with the vascular system. The heating coil has a proximal and distal end. The proximal end is coupled to the delivery wire and further comprises an uninsulated coil coupled to the distal end of the heating coil. The electrical resistance of the uninsulated coil is less than the heating coil so that substantially all of the heat generated by the current is generated within the insulated heating coil. The uninsulated coil serves as an endovascular electrode to provide completion of circuit through the delivery wire, and heating coil to the body electrode.

The improvement further comprises a current source coupled to the delivery wire for controllably delivering the electrical current thereto.

The invention is further defined as a method for forming coagulation of blood at a predetermined location within a vascular system. The method comprises the steps of disposing a microcatheter within the vascular system at the predetermined location and disposing from the microcatheter at the predetermined location at least one insulated heating coil. The insulated heating coil is electrically coupled to an insulated delivery wire included within the microcatheter and extends exteriorly to the vascular system. An electrical current delivery wire to the delivery wire to the heating coil to heat fluid within the vascular system at the predetermined location to thermally form a thrombus thereat. * As a result, thermal formation of a thrombus within the vascular system is selectively formed.

In the illustrated method at least two insulated heating coils connected together in an electrical circuit are disposed in the vascular system. Application of the current to the delivery wire and heating coil resistively generates substantially only within the heating coil.

In one embodiment the method further comprises applying current through the insulated heating coil to an uninsulated coil tip in electrical contact with the fluid in the vascular system to complete an electrical circuit through the delivery wire, heating coil and coil tip electrode to a body electrode in electrical communication with the vascular system.

The invention is still further characterized as a method for treating cancer comprising the steps of disposing a microcatheter within the vascular system at the predetermined location in a blood flow to a tumoral mass. At least one insulated heating coil is disposed from at by the microcatheter at the predetermined location. The insulated heating coil is electrically coupled to an insulated delivery wire included within the microcatheter and extends exteriorly to the vascular system. An electrical current is applied through the delivery wire to the heating coil to heat the blood flow within the vascular system at the predetermined location to thermally stress the tumoral mass downstream. As a result, thermal treatment of the tumoral mass is effected.

The invention and its various embodiments may be better visualized by turning to the following drawings wherein like elements are referenced by like numerals.

BRIEF DESCRIPTION OF THE DRAWINGS

FIG. 1 is a simplified diagrammatic side view of a catheter tip embodying the present invention.

FIG. 2 is a simplified diagrammatic side view of a second embodiment of the invention.

FIG. 3 is a simplified diagrammatic side view of a third embodiment of the invention.

FIG. 4 is a simplified view of a fourth embodiment of the invention.

FIG. 5 is an idealized diagram showing the placement of a catheter utilizing on of the embodiments of the invention within a vascular aneurysm.

FIG. 6 is a diagrammatic view of another embodiment of the invention showing utilization for cancer treatment.

FIG. 7a is a simplified cross sectional side view of an embodiment for use in a second technique in which the invention may be practiced.

FIG. 7b is a simplified side view of a catheter tip illustrated in a second embodiment also used in the second technique of the invention.

FIG. 8 is a simplified diagrammatic view which shows a source having a DC generator and an AC or RF generator coupled through a single pole, double throw switch to the delivery wire.

The invention and its various embodiments may now be understood by turning to the following detailed description.

DETAILED DESCRIPTION OF THE PREFERRED EMBODIMENTS

A clot is generated in an aneurysm, arteriovenous malformation or fistula by means of a catheter having an insulated heating coil coupled to an insulated delivery wire. In one embodiment, two delivery wires are coupled to heating coils to provide a closed circuit. The heating coils may be in the form of a double helix or a single helix in combination with a straight heating coil. The heating coils may be permanently connected to the delivery wires or may be electrolytically or mechanically detached therefrom.

Alternatively, a single insulated heating coil may be attached to a single insulated delivery wire with an uninsulated coil attached to the tip of the insulated heating coil. The electrical circuit is then made through the heating coil and non-insulated electrode coil into the vascular system and to a body electrode.

A catheter may also be used for heating blood within the vascular system which is directly flowed into a tumoral mass for the purposes of thermal treatment of cancer.

There are two main ways in which the goal of thermal thrombosis can be achieved in the invention, the first of which is illustrated in connection with FIGS. 1–6, which use some form of a double wire or closed circuit loop, and the second of which is illustrated in connection with the catheter tips shown in FIGS. 7a and 7b which uses some form of a single wire or body circuit loop.

Within each of these techniques, the invention may be practiced using a plurality of different embodiments or modifications. Further, the catheter tips of the methodology of the invention can be further be used not only for the promotion of clotting in aneurysms, arteriovenous malformations of fistulas, but also in therapeutic treatment of tumoral cells.

Consider first the first technique of endovascular promotion of the formation of clots as illustrated in FIGS. 1–5. As shown in FIG. 1, a catheter, generally denoted by reference numeral 10, is provided with two insulated stainless steel delivery wires 12 and 14 covered by insulating jackets 16. Additional catheter elements as are now known or later developed in the art may be included in the actual structure of the catheter, which is used. Delivery wires 12 and 14 are shown in isolation of the catheter assembly per se inasmuch as the remaining catheter structure is conventional and largely immaterial to the operation of the invention. However, it must be clearly understood that the delivery wires 12 and 14 are not necessarily disposed in the vascular system as a pair of associated wires as the simplified diagrammatic side views of FIGS. 1–4 might suggest. Instead, wires 12 and 14 would be appropriately included within a delivery or guide catheter of conventional design, which is symbolically denoted in FIG. 5 by reference numeral 22. Wires 12 and 14 could be coaxial.

Delivery wire 12 terminates at an end 18 of its insulating jacket 16 and is coupled at or near end 18 to a Teflon insulated platinum helix 20. The diameter of platinum helix 20 is typically in the range of 0.1 to 0.5 millimeters and may be comprised of a tight helical platinum wire, which when extended from the end of delivery catheter 22 as shown in FIG. 5, forms itself into a helical envelope as depicted by the large helical form in FIGS. 1–4.

Similarly, stainless steel delivery wire 14 terminates at its end 24 by connection to a Teflon insulated platinum helical coil 26 which, when released, also extends in the embodiment of FIG. 1 as a helix. Coils 20 and 26 thus form a pair of helical coils similar in gross geometry to the double helical coil of a DNA molecule. Helical coils 20 and 26 are coupled together at their distal ends 30, or may be fabricated from a single integral strand of coil, which is then bent or turned at end 30.

The connection between delivery wires 12 and 14 and helical coils 20 and 26, respectively, in the embodiment of FIG. 1 is by means of a permanent solder joint, although other types of mechanical and electrical connections are contemplated, some of which are described in the embodiments of FIGS. 2–4.

Further, in addition to generally forming a helical envelope as shown in FIG. 1, platinum coils 20 and 26 may be entirely or substantially limp, or without defined or prebiased form, so that a loose bird nest's configuration is formed by the released coils 20 and 26 as opposed to the tendency to form DNA-like double helix coil structures as shown in the embodiment of FIG. 1. In other words, coils 20 and 26 may or may not retain some type of geometric association with each other after being disposed out of the end of catheter 22 depending on the embodiment utilized.

The electrical resistance of platinum or the platinum tungsten alloy from which coils 20 and 26 are fabricated is typically much higher than that of the stainless steel delivery wires which comprise wires 12 and 14. possible to apply an electrical current to the double helical tip 28, which is comprised of coils 20 and 26, to selectively cause tip 28 to thermally heat with substantially no heat produced in delivery wires 12 and 14, because of the large disparity in the resistance between the two.

The electrical current applied to coil tip 28 through delivery wires 12 and 14 may be a DC current, alternating current, a radiofrequency power signal or any combination of the same. Regardless of the frequency of the electrical current, the current signal may have any envelope desired or be modulated in any way desired including modulation in the form of sine waves, square waves, triangular waves, pulsed, continuous or the like.

Coils 20 and 26 are Teflon coated or provided with another biologically nontoxic insulating material to prevent electrical shorting between coils 20 and 26 at any point. The solder connections in the embodiment of FIG. 1 between delivery wires 12 and 14 and coils 20 and 26, respectively, may similarly be insulated or placed at different longitudinal positions with respect to ends 18 and 24 of insulation 16 in order to avoid or to assist in avoiding short circuits between the solder connections.

The embodiment of FIG. 2 illustrates catheter 10 again in simplified side view and is identical in all respects to the embodiment of FIG. 1 with the exception that coil 26 has been replaced by a Teflon coated straight platinum wire 32. Although wire 32 is shown in FIG. 2 as straight, it must be understood that wire 32 typically has a diameter of 0.025 to 0.25 millimeters and can, in fact, be quite flexible and limp. On the other hand, the stiffness of wire 32 both by its solid geometric cross section, as well as by choice of the platinum-tungsten alloy, can be chosen to have a variety of different stiffnesses as may be desired in order to provide a degree of steerability of tip 28, controlled flexibility or malleability for disposition into the target body cavity.

A third embodiment of catheter 10 is illustrated in the simplified side view of FIG. 3. Again, catheter 10 of FIG. 3 is identical in all respects to the embodiment of FIG. 1 with the exception that coils 20 and 26 are connected to delivery wires 12 and 14 by means of corresponding temporary or detachable junctions 34. Tip 28 is preferably electrolytically detachable by applying a DC current between delivery wires 12 and 14 and a ground electrode 54, typically applied to an exterior body site and catheter 10 is disposed within the vascular system of a patient as shown in FIG. 5. The detailed nature of the electrolytic detachment of tip 28 as shown in FIG. 3 is described in greater detail in Guglielmi et al., "Endovascular Electrolytically Detachable Guidewire Tip for the Electroformation of Thrombus in Arteries, Veins, Aneurysms, Vascular Malformations and Arteriovenous Fistulas," U.S. Pat. No. 5,122,136 (1992), incorporated herein by reference. Alternative means of both electrical and mechanical detachment are contemplated within the invention and are further described in U.S. Pat. No. 5,122,136 (1992) and U.S. Pat. No. 5,354,295 (1994) each of which are similarly incorporated by reference.

Tip 28 is separated from wires 12 and 14 by electrolytic dissolution of junctions 34. Junctions 34, which are offset from each other to avoid contact with each other, are uninsulated and thus exposed to the blood stream so that they may be electrolytically corroded away at the defined location of the junction and coils 20 and 26 separated from delivery wires 12 and 14. Delivery wires 12 and 14 are thereafter removed, leaving tip 28 embedded in the thrombus thermally formed within the vascular cavity.

Another embodiment is depicted in the side view of FIG. 4. Catheter 10 of the embodiment of FIG. 4 is substantially identical to the embodiment of FIG. 2 with the exception that coils 20 and 32 are coupled to delivery wires 12 and 14, respectively, through temporary junctions 34 of the type described in connection with the embodiment of FIG. 3.

The embodiments of FIGS. 1–4 are employed in the vascular system of a patient as diagrammatically depicted in FIG. 5. The proximal end of delivery wires 12 and 14 are coupled to a signal or power source, generally denoted by reference numeral 36. In the illustrated embodiment of FIG. 5, source 36 is diagrammatically shown as symbolically including the double pole, double throw switch 38 for selectively coupling either a DC generator 40 or an AC or RF generator 42 to delivery wires 12 and 14. Switch 38 may be of any form, including a solid state switch. Source 36 is a conventional power source and may provide a current for the electrolytic detachment, electrolytic formation of thrombus, and/or thermal formation of thrombi utilizing conventional circuitry or such circuits later devised. As a consequence, further details concerning source 36 will not be discussed.

Catheter 10 is endovascularly disposed within the patient's vascular system using conventional medical techniques. Tip 28 is disposed in a vascular aneurysm, arteriovenous malformation or fistula, symbolically denoted by reference numeral 44, and illustrated in the embodiment of FIG. 5 as a wide-necked aneurysm 44 having an aneurysm opening or neck approximately 4 millimeters or greater. The apparatus and methodology of the invention is useful without limitation in aneurysms, malformations and fistulas without limitation, but is shown in connection with a wide-necked aneurysm 44 as being used to particular advantage.

Catheter 10 is disposed through vessel 48 into neck 46 to form a hairball or bird nest of coils comprising tip 28. Tip 28 is substantially proportionally longer then what is suggested in the simplified depictions of FIGS. 1–4, which, for the sake of simplicity, show tip 28 in a shortened form or at least in a much enlarged scale compared to that of FIG. 5. Typically tip 28 is 40 mm to 300 long while delivery wires 12 and 14 with microcatheter 22 may be 1000 to 1500 mm long. Coil tip 28 is thus delivered into aneurysm 44 by use of microcatheter 22 which is then withdrawn from aneurysm 44 into front vessel 48 providing the configuration as illustrated in FIG. 5. Therefore, a portion of delivery wires 12 and 14 are disposed in front vessel 48 such that in the embodiment of FIGS. 3 and 4, junctions 34 are disposed in or near aneurysm 44 or its neck 46. Junction 34 is easily detected through fluoroscopy techniques due to the greater radio-opacity of platinum as opposed to stainless steel.

A second microcatheter 50 is then disposed into vessel 48 which carries a detachable balloon 52. Balloon 52 is positioned next to neck 46 of aneurysm 48 and temporarily inflated in front vessel 48 to substantially seal across aneurysm neck 46 as depicted in the configuration of FIG. 5 or at least to substantial reduce or stop the blood flow past neck 46. Balloon 52 halts the flow of blood allowing the heat that is generated within aneurysm 44, when coil tip 28 is electrically heated, to be trapped within aneurysm 44. In many, if not most, instances, if no blood flow arrest were provided in vessel 48, the heat would be carried away by the blood flow and the formation of the thrombus substantially impeded. However, this is not always the case, and in some applications the use of balloon 52 is unnecessary. It is anticipated that in other applications, such as narrow necked aneurysms or appropriately shaped vasculated fistulas or malformations, the use of balloon 52 may not be necessary.

An alternating electric current, typically in the range of 20–40 volts at 40–60milliamps, is then applied to the proximal ends of delivery wires 12 and 14 through switch 38 from source 36. Platinum tip 28 disposed within aneurysm 44 becomes heated and in turn heats the blood within aneurysm 44 to achieve an intra-aneurysmal thrombosis. Various ways of monitoring the intra-aneurysmal temperature can be utilized and incorporated into the design of coil tip 28. For example, the resistance of the platinum tungsten alloy is a function of its temperature which may be monitored by appropriate conventional resistance detector within source 36. Thermal energy dosages can be determined by temperature and time measurements.

Once thrombosis has been achieved, delivery wires 12 and 14 are then coupled by means of switch 38 to DC generator 40. Typically, direct current of 1 milliamp at 2.5 volts is then applied from DC generator 40 through delivery wires 12 and 14 in parallel, utilizing a body electrode 54 as the opposite DC electrode. Junctions 34 thus become electrolytically dissolved so that the platinum tungsten tip 28 now embedded in the clotted aneurysm is detached from catheter 10. Catheter 10 and delivery wires 12 and 14 are then pulled away with balloon 52 deflated and similarly removed.

While the embodiments of FIGS. 3 and 4 are described as being used in a method for thrombus formation in FIG. 5, any of the embodiments of the invention and, in particular the embodiments of FIGS. 1 and 2, may be utilized in applications where endovascular blood heating is needed. FIG. 6 illustrates one such application used for therapeutic treatment of tumoral cells. In the embodiment of FIG. 6, coil tip 28 of catheter 10 is endovascularly disposed within a vessel 56 which leads, for example, into a vasculated tumoral mass 58. Blood flows in vessel 56 in the direction indicated by arrow 60. AC or RF current is then applied to tip 10 providing a controlled degree of heating of blood 60 such that the heated blood is then delivered to tumoral mass 58. Typically, the blood delivered to mass 58 may only be heated by 42 to 47 degrees centigrade to have therapeutic effect. The temperature elevation is sufficient for many types of cancers to destroy the tumoral cells. It is further expressly contemplated that the tumoral cells may be tagged or treated to specifically absorb a thermally activated agent that will assist in the destruction of the cell, such as by a thermal cyanin acting in a manner similar to photocyanins. Further, synergistic treatment of tumoral mass 58 is contemplated by combining thermal treatment as described in FIG. 6 with simultaneous or sequential chemotherapy or radiation.

FIGS. 7a and b illustrate additional embodiments of catheter 10 utilized in the second technique of the invention. In the embodiment of FIG. 7a, a single helical platinum-tungsten coil 62 having a Teflon or other insulating coating thereon is temporarily coupled by means of a detachable junction 64 to a single stainless steel delivery wire 66, which is disposed within an insulated jacket 68. Again, insulated wire 66 may be disposed within a delivery microcatheter or other catheter assembly as is conventionally used. The distal end 70 of the insulated platinum-tungsten coil 62 is permanently connected, such as by soldering, to an uninsulated platinum-iridium coil 72. Coil 72 is typically shorter in length than coil 62. Coil 72 serves as an electrode for contact with the blood or body tissue for completion of the circuit to a body electrode 54. Platinum-tungsten coil 62 typically has a substantially higher electrical resistance than either platinum iridium coil 72 or stainless steel wire 66, so that substantially all the heating is in coil 62.

The embodiment of FIG. 7b is identical to that described in connection with FIG. 7a with the exception that temporary detachable junction 64 is replaced by permanent or soldered junction 74.

Catheters 10 of FIGS. 7a and 7b are employed in a manner as illustrated in connection with FIG. 8. FIG. 8 is a simplified diagrammatic view which again shows a source 36 having a DC generator 40 and an AC or RF generator 42 coupled through a single pole, double throw switch 76 to delivery wire 66. In the embodiment of FIG. 8, AC or RF generator 42 has its opposing electrode coupled to body electrode 54.

Coil tip 28 is comprised in the embodiments of FIGS. 7a and 7b of coil tip portions 62 and 72 and is disposed by means of microcatheter 22 into vessel 78 and then coupled by means of switch 76 to generator 42. The current is then applied to delivery wire 66 and current flows to coil tip 28 and thence to uninsulated platinum iridium coil 72, which is the only portion of tip 28 in electrical contact with the blood or body fluids. The only portion of current tip 28 which heats to any substantial extent is the platinum tungsten portion, coil 62, because of its relative high electrical resistance.

If catheter 10 is used to occlude an aneurysm, then coil 62 and 72 of tip 28 are then both exposed within the aneurysm and electrolytically detached utilizing the embodiment of FIG. 7a. However, if catheter 10 is used to heat the blood, such as for tumoral treatment as shown in FIG. 6, then the embodiment of FIG. 7b is preferably used.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result.

In addition to the equivalents of the claimed elements, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. An endovascular device for use within a vascular system comprising:
    at least one delivery wire having a first resistance; and
    at least one detachable heating coil having a second resistance coupled to said delivery wire, said first resistance being less than said second resistance, wherein said delivery wire and heating coil are both electrically insulated to permit endovascular disposition of said delivery wire and heating coil into said vascular system for the purpose of delivering heat to a fluid within said vascular system at a predetermined location, substantially all of said heat being generated by electrical current flowing flowing within said heating coil rather than within said delivery wire,
    whereby endovascular thermal treatment is provided within said vascular system.

2. The endovascular device of claim 1 wherein said delivery wire and heating coil are temporarily coupled to each other and can be selectively detached while disposed in said vascular system.

3. The endovascular device of claim 2 wherein said delivery wire and heating coil are electrolytically detachable from each other.

4. The endovascular device of claim 2 wherein said delivery wire and heating coil are mechanically detachable from each other.

5. The endovascular device of claim 1 further comprising at least two delivery wires and at least two heating coils each having a proximal and distal end, said proximal end of each of said heating coils being coupled to corresponding ones of said two delivery wires, said distal end of said two heating coils being coupled together to provide a continuous circuit through a first one of said two delivery wires to a first one of said two heating coils, to a second one of said two heating coils, and to a second one of said two delivery wires.

6. The endovascular device of claim 5 wherein said two heating coils are each helical and together form a double helical tip.

7. The endovascular device of claim 6 wherein said two delivery wires and two heating coils are temporarily coupled to each other, each one of said two delivery wires being coupled to one of said two heating coils, and wherein said temporarily coupled delivery wire and heating coil can be selectively detached from each other while within said vascular system.

8. The endovascular device of claim 6 where each one of said two delivery wires are coupled to one of said two heating coils, wherein each one of said two delivery wires and said two heating coils are electrolytically detachable from each other.

9. The endovascular device of claim 5 wherein one of said two delivery wires is helical and the other one of said two delivery wires is nonhelical.

10. The endovascular device of claim 7 where each one of said two delivery wires are coupled to one of said two heating coils, wherein each one of said two delivery wires and said two heating coils are temporarily coupled to each other and can be selectively detached from each other.

11. The endovascular device of claim 9 where each one of said two delivery wires are coupled to one of said two heating coils, and wherein each one of said two delivery wires and said two heating coil are electrolytically detachable from each other.

12. The endovascular device of claim 1 further comprising a body electrode adapted to be in electrical circuit with said vascular system and with said delivery wire, wherein said heating coil has a proximal and distal end, said proximal end being coupled to said delivery wire and further comprising a uninsulated coil coupled to said distal end of said heating coil, said uninsulated coil having an electrical resistance, said electrical resistance of said uninsulated coil being less than said heating coil so that substantially all of said heat generated by said current is generated within said heating coil, said uninsulated coil serving as an endovascular electrode to provide completion of circuit through said delivery wire and heating coil.

13. The endovascular device of claim 12 wherein said delivery wire and heating coil are temporarily coupled to each other and can be selectively detached within said vascular system.

14. The endovascular device of claim 12 wherein said delivery wire and heating coil are electrolytically detachable from each other.

15. The endovascular device of claim 1 further comprising a current source to said delivery wire for controllably delivering said electrical current thereto.

16. A method for forming a thrombus at a predetermined location within a vascular system comprising:
    disposing a microcatheter within said vascular system at said predetermined location;
    disposing from said microcatheter at said predetermined location at least one insulated heating coil, said insulated heating coil being electrically coupled to an insulated delivery wire included within said microcatheter and extending exteriorly to said vascular system;
    applying electrical current through said delivery wire to said heating coil to heat fluid within said vascular system at said predetermined location to thermally form a thrombus thereat; and
    detaching said delivery wire from said heating coil; and
    withdrawing said microcatheter and delivery wire from said vascular system,
    whereby thermal formation of a thrombus within said vascular system is selectively formed.

17. The method of claim 16 where disposing a heating coil in said vascular system comprises disposing at least two insulated heating coils connected together in an electrical circuit.

18. The method of claim 16 where applying said current to said delivery wire and heating coil resistively generates heat substantially only within said heating coil.

19. The method of claim 16 where applying current to said delivery wire and heating coil further comprises applying current through said heating coil to an uninsulated coil tip electrode in electrical contact with said fluid in said vascular system to complete an electrical circuit through said delivery wire, heating coil and coil tip electrode to a body electrode in electrical communication with said vascular system.

* * * * *